(12) United States Patent
Allen et al.

(10) Patent No.: US 7,250,284 B2
(45) Date of Patent: Jul. 31, 2007

(54) DESTABILIZED BIOLUMINESCENT PROTEINS

(75) Inventors: Michael S. Allen, Knoxville, TN (US); Gupta Rakesh, New Delhi (IN); Sayler S. Gary, Blaine, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/827,133

(22) Filed: Apr. 19, 2004

(65) Prior Publication Data

US 2004/0209302 A1 Oct. 21, 2004

Related U.S. Application Data

(60) Provisional application No. 60/463,851, filed on Apr. 18, 2003.

(51) Int. Cl.
   *C12N 15/00* (2006.01)
   *C12N 1/21* (2006.01)
   *C12N 5/00* (2006.01)
   *C07H 21/00* (2006.01)

(52) U.S. Cl. ............... 435/252.3; 536/23.4; 435/320.1; 435/254.11; 435/325

(58) Field of Classification Search .................... None
   See application file for complete search history.

(56) References Cited

OTHER PUBLICATIONS

Leclerc et al. Development of a destabilized firefly luciferase enzyme for measurement of gene expression. Biotechniques. vol. 29, No. 3, pp. 590-601, Sep. 2000.*

Andersen et al. New unstable variants of green fluorescent protein for studies of transient gene expression in bacteria. Appl Environ Microbiol. vol. 64, No. 6, pp. 2240-2246, Jun. 1998.*

Hakkila et al. Reporter genes lucFF, luxCDABE, gfp, and dsred have different characteristics in whole-cell bacterial sensors. Anal Biochem. vol. 301, No. 2, pp. 235-242, Feb. 2002.*

Vieites et al. Expression and in vivo determination of firefly luciferase as gene reporter in *Saccharomyces cerevisiae*. Yeast. vol. 10, No. 10, pp. 1321-1327, Oct. 1994.*

Mateus et al. Destabilized green fluorescent protein for monitoring dynamic changes in yeast gene expression with flow cytometry. Yeast. vol. 16, No. 14, pp. 1313-1323, Oct. 2000.*

Berset et al. Transferable domain in the G(1) cyclin Cln2 sufficient to switch degradation of Sic1 from the E3 ubiquitin ligase SCF(Cdc4) to SCF(Grr1). Mol Cell Biol. vol. 22, No. 13, pp. 4463-4476, Jul. 2002.*

Knudsen et al. tmRDB (tmRNA database). Nucleic Acids Res. vol. 29, No. 1, pp. 171-172, Jan. 2001.*

Lucy Ghoda et al.: "Trypanosome Ornithine Decarboxylase is stable . . . "; The Journal of Biological Chemistry, vol. 265, No. 20, Issue of Jul. 15, 1990, pp. 11823-11826.

Xianqiang Li et al.: "Generation of Destabilized Green Fluorescent . . . ", The Journal of Biological Chemistry, vol. 273, No. 52, Dec. 25, 1998, pp. 34970-34975.

Nelly Valkova et al.: "Control of Luminescence Decay and Flavin Binding . . . "; Biochemsitry, 38, 1999, pp. 13820-13828.

* cited by examiner

*Primary Examiner*—Celine Qian
*Assistant Examiner*—Jennifer Dunston
(74) *Attorney, Agent, or Firm*—Ruden McClosky; Stanley A. Kim

(57) ABSTRACT

Purified nucleic acids, vectors and cells containing a gene cassette encoding at least one modified bioluminescent protein, wherein the modification includes the addition of a peptide sequence. The duration of bioluminescence emitted by the modified bioluminescent protein is shorter than the duration of bioluminescence emitted by an unmodified form of the bioluminescent protein.

14 Claims, 3 Drawing Sheets

DESTABILIZED BIOLUMINESCENT PROTEINS

CROSS REFERENCE TO RELATED APPLICATIONS

The present application claims the priority of U.S. provisional patent application No. 60/463,851, entitled "Destabilized Lux," filed Apr. 18, 2003. The foregoing is herein incorporated by reference in its entirety.

STATEMENT REGARDING FEDERALLY SPONSORED RESEARCH

This invention was made with U.S. government support under grant number ROI 2580 127 awarded by the Department of Energy. The U.S. government may have certain rights in the invention.

FIELD OF THE INVENTION

The invention relates generally to the fields of molecular biology, microbiology, and micro-processing. More particularly, the invention relates to expression in prokaryotic and eukaryotic cells of genes encoding variants of bioluminescent proteins having shorter half lives. of luminescence than their wild-type counterparts.

BACKGROUND

Bioluminescence refers to the production of light by a chemical reaction that originates in a living organism. Primarily a marine phenomenon, bioluminescence is observed in a broad variety of organisms ranging from bacteria to fish, crustaceans and squid, but is primarily attributable to chemical reactions that occur in bacteria and dinoflagellates. Among land dwelling organisms, bioluminescence is found among certain centipedes, millipedes and insects such as fireflies and click beetles but is unknown in plants, birds, reptiles, amphibians and mammals.

Genes responsible for the production of bioluminescent proteins have been isolated by molecular cloning techniques, leading to the widespread and expanding use of such proteins in a variety of applications including, inter alia, use as: 1) bioreporters for detection of environmental compounds, 2) reagentless components in bioelectronic devices, 3) whole cell logic gates for biocomputing, 4) tools for in situ functional imaging, 5) markers of recombinant strains released into the environment, and 6) markers to enable in vivo imaging of bacteria during systemic infection in animal hosts (Applegate et al., Appl. Environ. Microbiol., 64:2730-2735, 1998; Sayler, G. S., and Ripp, S., Current Opinion in Biotechnology, 11:286-289, 2000; and Liu et al., Plasmid, 44:250-261, 2000).

Luciferases of the lux family (Lux) are bioluminescent proteins derived from certain bioluminescent bacterial strains that have found widespread use in various applications. Lux is the product of the luxAB genes, which encode luciferase, a heterodimeric bioluminescent catalyzing enzyme. The entire luxCDABE cassette has been isolated from several bioluminescent bacteria including *Vibrio fischeri*, *V. harveyi*, and *Photorhabdus luminescens*. Use of the complete operon of bacterial luciferase (i.e., luxCDABE) has enabled construction of self-sufficient bioreporters containing all of the required elements for production of light in response to specific chemicals or physical agents.

Despite these considerable advances, currently available bioreporters based on luxCDABE are not ideally suited for applications requiring a relatively short half life of the reporter protein. As one example, the duration of Lux emission by existing bioreporters limits their usefulness for monitoring certain events in real time, such as both initiation and termination of transcription in a cell. Additionally, in applications using bioreporters in synthetic gene circuits, the long time constants associated with decay of presently available reporter proteins can significantly degrade circuit performance.

SUMMARY

The invention relates to modified lux-based nucleic acid and vector compositions as well as bioreporter cells, both prokaryotic and eukaryotic, incorporating these compositions. The modified Lux proteins emit bioluminescence with a duration shorter than that of conventional lux-based bioreporters. More specifically, the bioreporters are engineered to express variants of LuxA and LuxB proteins that are rapidly degradable via cellular proteolytic pathways and mechanisms, such as by tail-specific proteases in bacterial cells and by a ubiquitin-proteasome pathway in eukaryotic cells. Degradation of the modified bioluminescent proteins reduces the duration of the bioluminescent response produced upon stimulation by an effector molecule. This feature is advantageous for a wide variety of real-time or temporally responsive biosensing, biocomputing, and Lux array technologies.

Accordingly, in one aspect the invention includes a purified nucleic acid construct including a gene cassette encoding at least one modified bioluminescent protein. The modified protein can contain at least one modification in its amino acid sequence relative to the sequence of an unmodified form of the same protein, wherein the modification includes the addition of a peptide sequence to the protein. The addition of the peptide sequence reduces a first duration of bioluminescence emitted by the modified bioluminescent protein relative to a second duration of bioluminescence emitted by the unmodified form of the protein.

In preferred embodiments of the purified nucleic acid construct, the gene cassette encodes a luciferase protein. The luciferase protein can include at least one a Lux protein selected from Lux A and Lux B. The Lux protein can include the amino acid sequence of a Lux protein isolated from bacterial strains including *Photorhabdus luminescens*, *Vibrio fischeri* and *Vibrio harveyi*.

In some versions of the nucleic acid, the gene cassette can encode all proteins necessary for production of bioluminescence without addition of an exogenous substrate. For example, the purified nucleic acid construct can include a lux CDABE cassette. Other versions of the cassette requiring addition of exogenous substrate can include, for example, only a bioluminescent protein such as luciferase.

The modified form of the bioluminescent protein encoded by the nucleic acid of the invention can include the addition of a peptide sequence that specifically binds to a protein associated with a proteolytic pathway.

The protein associated with a proteolytic pathway can be a tail-specific protease. In particular embodiments based on tail-specific proteases, the peptide sequence of the modified bioluminescent protein can include the amino acid sequences of SEQ ID NOS:8-10. In particular embodiments using Lux proteins, these peptide sequences can be added to one or both of LuxA and Lux B.

In other versions of the nucleic acids of the invention, the protein associated with a proteolytic pathway can be one that mediates degradation of the modified bioluminescent protein via a ubiquitin-proteasome pathway. The protein that mediates degradation via this pathway can be SCF(Grr1). In a preferred embodiment utilizing this pathway, the peptide sequence of the modified bioluminescent protein can include a PEST-rich sequence. The PEST-rich sequence can be a carboxy terminus of G1 cyclin (Cln2).

Another aspect of the invention is a vector including a gene cassette encoding at least one modified bioluminescent protein. The modified protein can contain at least one modification in its amino acid sequence relative to the sequence of an unmodified form of the same protein, wherein the modification includes the addition of a peptide sequence to the protein. The addition of the peptide sequence reduces a first duration of bioluminescence emitted by the modified bioluminescent protein relative to a second duration of bioluminescence emitted the unmodified form of said protein.

The vector can be a plasmid.

The vector can be an expression vector suitable for driving expression in a cell type such as a bacterial cell, a yeast cell or a mammalian cell.

Yet a further aspect of the invention is a cell expressing the vector of the invention. The cell can be a prokaryotic cell, for example a bacterial cell. Preferred embodiments of the prokaryotic cells harbor a vector that includes the purified nucleic acid of claim 7 or 8.

The cell can also be a eukaryotic cell such as a yeast cell or a mammalian cell.

The modification in the purified nucleic acid reduces a first duration of bioluminescence emitted by the modified protein relative to a second duration of bioluminescence emitted by the unmodified protein. The duration of bioluminescence can be determined by comparing a time course of a first measure of bioluminescence emitted by the modified protein and a time course of a second measure of bioluminescence emitted by the unmodified protein. The first measure can be between about 100-fold and 1000-fold lower than the second measure.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference for the proposition cited. In the case of conflict, the present specification, including any definitions will control. The particular embodiments discussed below are illustrative only and not intended to be limiting.

The term "bioreporter," as used herein, refers to a biological system or organism that has been adapted or engineered to produce a detectable response in the presence of a selected compound or condition.

As used herein, "luminescence" refers to the production and/or emission of light by a chemical or electrical process, but not from a thermal source such as incandescence.

The terms "bioluminescence," "bioluminescent," and "bioluminesce" refer to luminescence that occurs in a living organism, for example in a photogenic organism, in which energy from a chemical reaction is transformed into light energy. An example of a bioluminescent chemical reaction is a reaction in which a chemical substrate such as luciferin reacts with oxygen in the presence of an enzyme, for example luciferase. "Bioluminescence" "bioluminescent," and "bioluminesce" also refer to the production of light using chemical reagents and reactions that produce bioluminescence in nature; in other contexts. As an example, bioluminescence may occur in vitro, or in a recombinant organism engineered to contain the chemical reagents necessary for bioluminescence in a naturally occurring organism.

"Fluorescence," as defined herein, refers to luminescence in the form of secondary light that is generated upon exposure to a primary light source. A substance emits light by "fluorescence" when it absorbs incident radiation at a first (i.e., excitation) wavelength and emits radiation at a second, usually different (i.e., emission) wavelength. Fluorescent emission ceases when the incident radiation ends. Accordingly, the mechanism of production of light by "bioluminescence" is distinct from the mechanism of production of light by "fluorescence."

The terms "LuxCDABE" and "LuxCDABE cassette" refer to an operon containing five genes necessary for self-sustained bioluminescence in bacteria. LuxAB is a luciferase which catalyzes the light-producing reaction. LuxCE is a multi-component enzyme that converts myristic acid to a fatty aldehyde substrate for the light-producing reaction, with the assistance of a transferase, i.e., LuxD.

A "proteolytic pathway," as used herein, refers to a series of enzymatic or chemical steps by which a protein can be degraded in a cell into its constituent parts by one or more proteolytic enzymes.

The term "tail specific protease" refers to a class of proteolytic enzymes that recognize non-polar amino acid residues in the carboxy terminal end of another protein, and catalyze the degradation of the protein.

A "ubiquitin-proteasome pathway," as herein defined refers to a series of steps leading to degradation within a cell of a protein containing a PEST sequence that is recognized and ubiquinated, thereby marking it for degradation by a proteasome. The term "proteasome," as used herein, refers to an ATP-dependent multi-enzyme complex, variably composed of several subunits and located within the cytoplasm and/or nucleus of a cell, that is involved in selective protein degradation.

The term "vector," as used herein refers a vehicle used for the introduction of a nucleic acid, such as a recombinant DNA molecule, into a host. A vector may be a plasmid, a transposon, a virus, or any other suitable vehicle. An "expression vector" refers to a vector containing a nucleic acid, for example a DNA molecule encoding a gene product of interest, and further including regulatory elements useful for the expression of a gene product in a host, including but not limited to a promoter and a termination sequence.

Other features and advantages of the invention will be apparent from the following detailed description, and from the claims.

DETAILED DESCRIPTION

Figure 1:
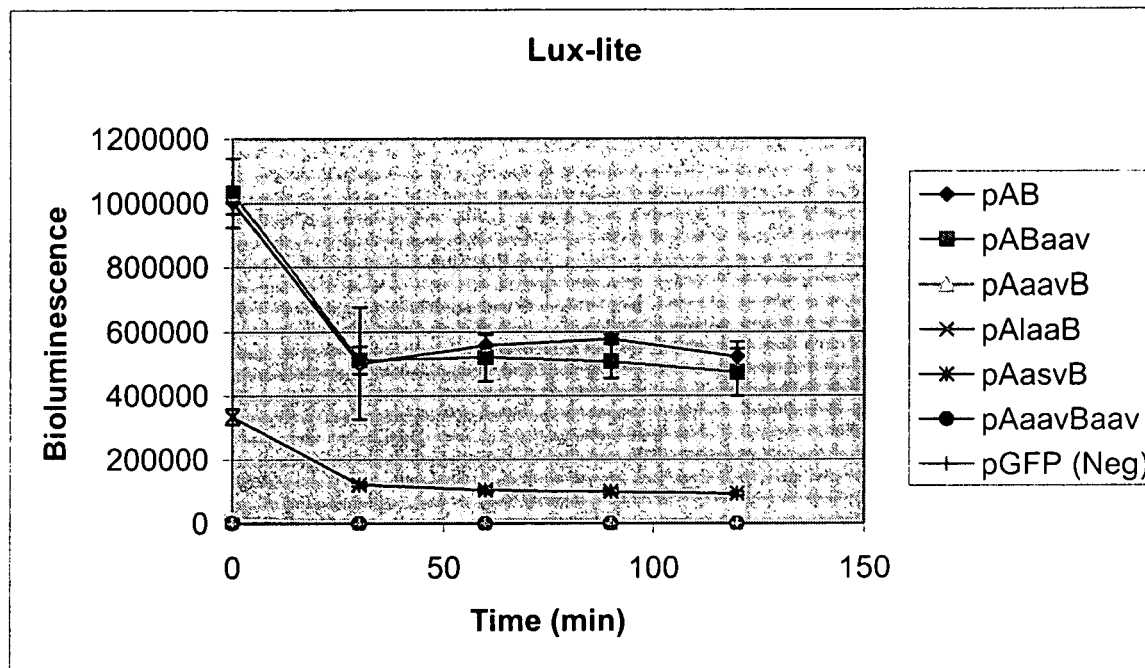
FIG. 1 is a graph showing changes in bioluminescence over time, in transformed *E. coli* cells following various periods of inhibition of transcription and translation.

The invention relates to purified nucleic acid constructs that include a gene cassette encoding at least one modified bioluminescent protein. The modified protein contains a modification in its amino acid sequence, relative to the sequence of an unmodified form of the same protein, that causes the duration of bioluminescence emitted by the modified protein to be shorter than the duration of bioluminescence emitted by an unmodified form of the same protein.

Biological Methods

Methods involving conventional molecular biology techniques are described herein. Such techniques are generally known in the art and are described in detail in methodology treatises such as Molecular Cloning: A Laboratory Manual, $3^{rd}$ ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

Methods involving conventional biology and microbiology are also described herein. Such techniques are generally known in the art and are described in detail in methodology treatises such as Sambrook et al., supra; Current Protocols in Molecular Biology, ed. Ausubel et al., Greene Publishing and Wiley-Interscience, New York, 1992 (with periodic updates); Techniques in Microbial Ecology, ed. Robert S. Burlage et al., Oxford University Press, New York, N.Y., 1998; Environmental Microbiology, ed. Raina M. Maier, Academic Press, Burlington, Mass., 2000; and Environmental Molecular Microbiology: Protocols and Applications, ed. Paul. A Rochelle, Bios Scientific Publishing, Ltd., Oxford, UK, 2001. Methods involving culturing and manipulation of yeast cells are described in Methods In Yeast Genetics: A Cold Spring Harbor Laboratory Course Manual, 2002, Cold Spring Harbor Laboratory Press, Cold Spring Harbor, N.Y. Methods for measuring bioluminescence, for example using a luminometer, are well known in art and are generally described in treatises such as Physical Optics and Light Measurements (Methods of Experimental Physics), Vol. 26, 1989, Daniel Malacara, ed., Academic Press.

Modified Bioluminescent Proteins

Modified bioluminescent proteins encompassed by the invention include any bioluminescent protein modified in such a way as to emit bioluminescence of shorter duration than that of the corresponding unmodified ("native" or "wild type") protein. The modification includes the addition of a peptide sequence to the amino acid sequence of the protein. Addition of the peptide reduces the duration of bioluminescence emitted by the modified bioluminescent protein, relative the duration of bioluminescence emitted by the same protein in unmodified form. The reduction in duration of bioluminescence can be determined, for example, by comparing a time course of a first measure of bioluminescence emitted by the modified protein with that of a second measure of bioluminescence emitted by the unmodified protein. The first measure can be between about 100-fold and 1000-fold, (i.e., about 200, 300, 400, 500, 600, 700, 800, 900, and 1000-fold) lower than the second measure of bioluminescence emitted by the unmodified form of the protein.

Those of skill in the arts of molecular and cellular biology will recognize that many schemes may be utilized to produce such a modified bioluminescent protein. One scheme for shortening the duration of the bioluminescent response is to reduce the overall numbers of bioluminescent protein molecules present in a cell at a given time by "destabilizing" these molecules, for example by targeting them for degradation within the cell. According to the foregoing strategy, one preferred embodiment of a modified bioluminescent protein of the invention is one in which the amino acid sequence of the modified protein includes a peptide that specifically binds to a protein associated with a proteolytic pathway that targets the modified protein for degradation.

The choice of cellular proteolytic pathway can be guided by the type of cell in which the bioreporter is constructed. For example, an exemplary proteolytic pathway in a bacterial cell involves the action of a class of enzymes termed "tail-specific proteases" (TSP) present in *Escherichia coli* and other gram-negative species (Silber K R et al., 1992, Proc Natl Acad Sci USA 89, 295-299; Keiler K C et al. Science 1996, 271:990-993; Keiler K C and Sauer R T J. Biol Chem 1996, 2589-2593). TSP enzymes catalyze the proteolysis of proteins containing certain peptide sequences in their carboxyl termini (tails) by specifically binding to those sequences, facilitating degradation of the bound protein by the protease. A naturally occurring protein degradation system in a bacterial cell, such as TSP, can therefore be exploited to degrade modified proteins in which a peptide sequence recognized by the enzyme has been incorporated into the amino acid sequence of the modified protein (Andersen, J B et al., Appl. Environ Microbiol 1998, 2240-2246; Elowitz, M B and S Leibler 2000. Nature 403:335-338).

In accordance with the above scheme for degradation of modified bioluminescent proteins, some embodiments of the modified bioluminescent proteins of the invention incorporate into the amino acid sequence of the protein a carboxyl-terminal tag recognized by a TSP enzyme. Specific examples of such proteins are described in examples below, and include modified versions of the bacterial luciferase holoenzyme LuxAB. Short half-life variants of LuxA and LuxB, along with a double-modified variant were constructed and cloned into *E. coli*.

Results of bioluminescence assays using transfected bacterial cells indicated that the addition of a carboxy-terminal tag decreased the functional half-life of the holoenzyme. In some embodiments of the modified bioluminescent proteins of the invention, the amino acid sequences of the protein includes peptides having sequences listed herein as SEQ ID NOS:8-10.

An exemplary proteolytic pathway that can be utilized in a eukaryotic cell, such as a yeast cell or a mammalian cell, is the ubiquitin-proteasome pathway. Degradation of proteins by this pathway in a mammalian cell, utilizing a motif known as "PEST," is described, for example, in Li X et al. 1998 J Biol Chem 273:34970-75. The ubiquitin-proteasome pathway in yeast is described, for example, in Berset C et al., Mol. Cell Biol 2002, 13:4463-76. Analyses of the molecular components of this pathway have led to the elucidation of a domain within the G1 cyclin Cln2 (PEST motif) that is recognized by a component of the ubiquitin-ligase complex within yeast cells, i.e., SCF(Grr1). Binding of the Cln2 domain to SCR(Grr1) causes a protein containing the Cln2 domain to be targeted for destruction by the ubiquitin-proteasome pathway. Accordingly, incorporation of a PEST-rich domain into a modified bioluminescent protein of the invention can target the modified protein for degradation by the ubiquitin-proteasome pathway. Methods for selecting particular PEST sequences useful for addition as "degradation domain" peptides are discussed, for example, in Li et al., supra, and in Mateus C and Avery S V, Yeast 2000, 16:1313-23. Embodiments of modified bioluminescent proteins based on utilization of the ubiquitin-proteasome pathway are further described in examples below.

Nucleic Acids, Vectors and Cells Including Constructs Encoding Modified Bioluminescent Proteins The invention further pertains to nucleic acid-based compositions including purified nucleic acids that encode the above-described modified bioluminescent proteins, vectors that incorporate these nucleic acids, and cells transformed with these vectors, causing the cells to express the modified proteins. Accordingly, one aspect of the invention is a purified nucleic acid construct that includes a gene cassette encoding at least one modified bioluminescent protein. The modified protein contains a modification in its amino acid sequence relative to the sequence of an unmodified form of the same protein, wherein the modification causes the duration of bioluminescence emitted by the modified protein to be shorter than the duration of bioluminescence emitted by an unmodified (wild-type) form of said protein. As described above, in preferred embodiments, the modifications involve additions (such as carboxyl tags) to the amino sequences of the proteins. Accordingly, the nucleic acids of the invention include those that encode the biololuminescent proteins modified to include such additional sequences.

General methods of making the various embodiments of the nucleic acid constructs of the invention in both prokaryotic cells (i.e., bacteria) and eukaryotic cells (i.e., yeast) are well known in the art of molecular biology. Specific examples related to modified Lux A and Lux B variants are described in detail in the examples below, and various starting materials are listed in Tables 1 and 2 infra.

Vectors of use in the invention are any that can be used to drive expression of the gene cassette of interest in an appropriate cell type. Many types of suitable vectors are commercially available and are well known to those of skill in the art of molecular biology. Examples of specific vectors that can be used in the practice of the invention are further described in the below examples.

EXAMPLES

The present invention is further illustrated by the following specific examples, which should not be construed as limiting the scope or content of the invention in any way.

Example 1

Materials and Methods for Construction of Destabilized Lux

Genetic constructs. Primers used in construction of the Lux variants are shown in Table 1. Wild type and modified variants of the luxA and B genes were amplified by PCR directly from *P. luminecens* genomic DNA (ATCC Accession No. 29999).

TABLE 1

Primers used in construction of Lux variants

| | | |
|---|---|---|
| LuxA forward: |     KpnI     Start<br>5'-GGTACC GC ATG AAA TTT GGA AAC TTT TTG-3' | (SEQ ID NO:1) |
| LuxB forward: |     XMaI            Start<br>5'-CCCGGG CT AAG GAG AAA GAA ATG AAA T-3' | (SEQ ID NO:2) |
| LuxB reverse: |       BamHI    Stop<br>5'-TTA GGATCC TA TTA G GTA TAT TCC ATG TGG TAC TTC-3' | (SEQ ID NO:3) |
| LuxAaav reverse: |       XmaI    Stop V  A  A<br>5'-TTA CCCGGG A CTA AAC TGC TGC AGC GTA GTT TTC GTC GTT<br>TGC TGC AGG CCT ATA TAA TAG CGA ACG TTG TTT-3' | (SEQ ID NO:4) |
| LuxAlaa reverse: |       XmaI    Stop A  A  L<br>5'-TTA CCCGGG A CTA AGC TGC TAA AGC GTA GTT TTC GTC GTT<br>TGC TGC AGG CCT ATA TAA TAG CGA ACG TTG TTT-3' | (SEQ ID NO:5) |
| LuxAasv reverse: |       XmaI    Stop V  S  A<br>5'-TTA CCCGGG A CTA AAC TGA TGC AGC GTA GTT TTC GTC GTT<br>TGC TGC AGG CCT ATA TAA TAG CGA ACG TTG TTT-3' | (SEQ ID NO:6) |
| LuxBaav reverse: |       BamHI   Stop V  A  A<br>5'-TTA GGATCC TA TTA AAC TGC TGC AGC GTA GTT TTC GTC GTT<br>TGC TGC AGG ACT GGT ATA TTC C ATG TGG TAC TTC-3' | (SEQ ID NO:7) |

Unique restriction sites used in the final assembly are underlined. Start and stop codons and pertinent amino acids are indicated above the respective sequences.

Bacterial strains and plasmids used in the construction of the Lux variants are shown in Table 2.

TABLE 2

Strains and plasmids used to construct Lux fusions

| Name | Properties | Source |
|---|---|---|
| *Escherichia coli* TOP10 | Cloning and expression strain | Invitrogen (Carlsbad, CA) |
| pCR2.1 | Am$^R$, Km$^R$ | Invitrogen |
| pZE21-GFPaav | Km$^r$; GFP-reporter plasmid. All | Elowitz and |

TABLE 2-continued

Strains and plasmids used to construct Lux fusions

| Name | Properties | Source |
|---|---|---|
| | subsequent plasmids used in this study were derived from this plasmid with the GFPaav removed and replaced with luxA and/or luxB variants. | Liebler |
| pAB | pZE21 with the wild-type luxAB of *P. luminescens* cloned in place of GFPaav. | This work |
| pAaavB | pZE21 containing the luxA gene modified to include the gene sequence of the 11-amino acid carboxy-terminal tag AANDENYAAAV (SEQ ID NO:8), and the wild type luxB. Estimated $t_{1/2}$ = 60 min. | This work |
| pAlaaB | pZE21 containing the luxA gene modified to include the gene sequence of the 11-amino acid carboxy-terminal tag AANDENYALAA (SEQ ID NO:9), and the wild type luxB. Estimated $t_{1/2}$ = 40 min. | This work |
| pAasvB | pZE21 containing the luxA gene modified to include the gene sequence of the 11-amino acid carboxy-terminal tag AANDENYAASV (SEQ ID NO:10), and the wild type luxB. Estimated $t_{1/2}$ = 110 min. | This work |
| pABaav | pZE21 containing the luxB gene modified to include the gene sequence of the 11-amino acid carboxy-terminal tag AANDENYAAAV (SEQ ID NO:8), and the wild type luxA. Estimated $t_{1/2}$ = 60 min. | This work |
| pAaavBaav | pZE21 containing the luxA and luxB genes modified to include the gene sequence of the 11-amino acid carboxy-terminal tag AANDENYAAAV (SEQ ID NO:8). | This work |

Wild type luxAB and luxABaav were amplified by PCR, gel purified, and cloned into the TOPO-TA cloning vector pCR2.1 (Invitrogen, Carlsbad, Calif.) according to the manufacturer's instructions.

For production of luxA variants, luxBaav, and wild-type luxB, the genes were independently amplified and cloned. The luxA variants were digested overnight with XmaI and XbaI and ligated upstream of the luxB or luxBaav genes in plasmid pCR2.1. The wild type luxAB and the newly assembled variants were then each digested overnight from their respective TA-cloning vectors with BamHI and KpnI, gel purified, and directionally cloned in place of the GFPaav gene of the repressilator reporter plasmid (Elowitz M B and Leibler S 2000. Nature 403:335-338). T4 DNA ligase was purchased from Fisher Scientific (Pittsburgh, Pa.), and all other enzymes were purchased from Promega (Madison, Wis.).

Example 2

Assay of Bioluminescence

Overnight cultures of the four Lux variants and a negative control carrying the parent vector with the gene for green fluorescent protein (GFP) were transferred into triplicate tubes of fresh LB medium containing 50 ug/mL kanamycin. Cultures were then grown to an optical density at 546 nm ($OD_{546}$) of ~0.6. Bioluminescence measurements were made at t=0 as described below. Subsequently, rifampicin (150 μg/mL) and tetracycline (30 μg/mL) were added to all cultures to block transcription and translation, respectively.

For bioluminescence measurements, samples of one mL volume were taken immediately (t=0) and at 30 min. intervals thereafter and assayed for $OD_{546}$ and bioluminescence. $OD_{546}$ was measured in a Beckman DU-640B spectrophotometer. Bioluminescence was assayed by first adding 10 μL of N-decanal (Sigma, St. Louis, Mo.) to the 1-mL samples, inverting 10 times, and measuring light with a SDI Deltatox handheld luminometer. Some assays were conducted with addition of bacteriostatic antibiotics to block transcription and translation (rifampicin and tetracycline, respectively), followed by monitoring bioluminescence in the presence of aldehyde over time. Three light measurements were taken in rapid succession and these values were averaged for each sample. Standard deviations between the averages of three independent samples were calculated.

Example 3

Lux-Based Bacterial Bioreporters Exhibiting Reduced Bioluminescent Half Life

Bioluminescence measurements were compared in *E. coli* strains harboring plasmids containing the wild type luxAB genes of *P. luminescens* (Meighen E A 1991 Microbiological Reviews 55:123-142) behind a constitutive promoter, and those containing luxA and luxB variants containing carboxy-terminal tags constructed as described above.

Referring to FIG. 1, the results showed that inhibition of transcription or translation resulted in a rapid decline in bioluminescence within 30 minutes ($t_{1/2}$) in cells expressing wild-type luxA (FIG. 1, pAB). The maximum bioluminescence at times t=0 are consistent with the quantity of luciferase expected to accumulate within the cells when being constitutively expressed. Luciferase with a short half-life does not accumulate to the same level as the wild-type, the decreases in half-life resulting in lower levels of bioluminescence at t=0).

Figure 2:
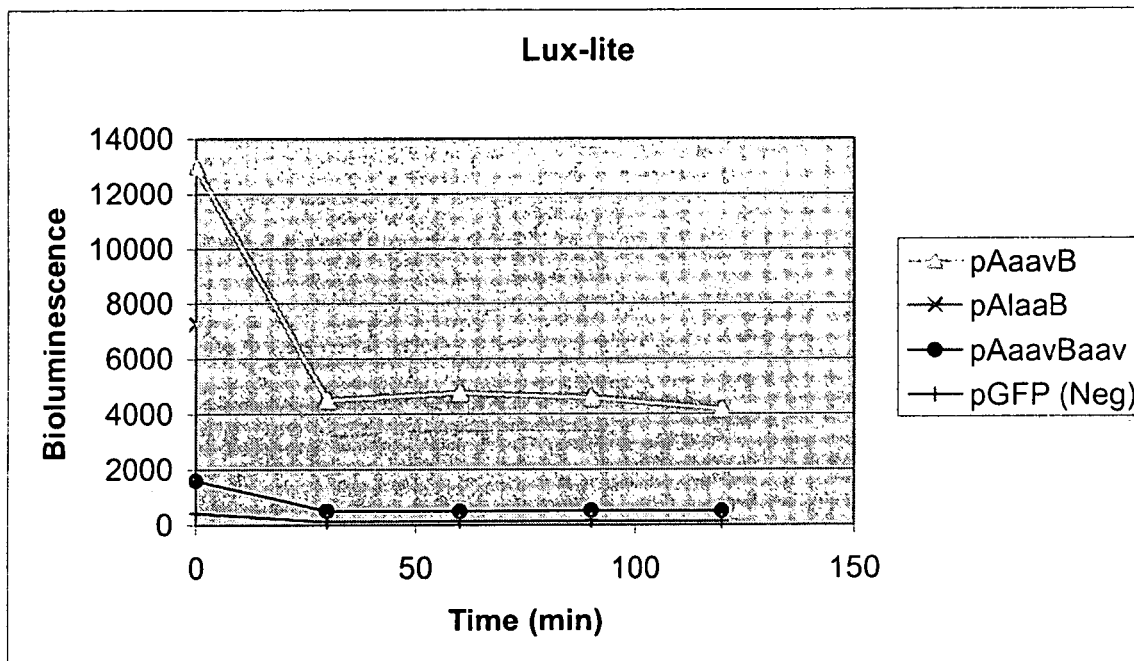
FIG. 2 is a graph showing expansion of the data in FIG. 1, illustrating bioluminescent behavior of constructs producing lower levels of light.

Modification of the LuxA protein by addition of the −aav tag to the luxA gene resulted in an approximate 100-fold decrease in bioluminescence at time $t_0$ (pAaavB in FIG. 1). An even more dramatic decrease in initial bioluminescence was observed when both LuxA and LuxB included the −aav tag (FIG. 1, pAaavBaav). The double modified holoenzyme produced bioluminescence nearly 1000-fold less than that of the wild type. (FIGS. 1 and 2). Unexpectedly, modification of the LuxB monomer alone (pABaav) did not result in decreased bioluminescence over time and did not decrease peak bioluminescence. Bioluminescence in this variant was found to be similar to that of the wild type (pAB) over the course of the experiments (FIG. 1).

Figure 3:
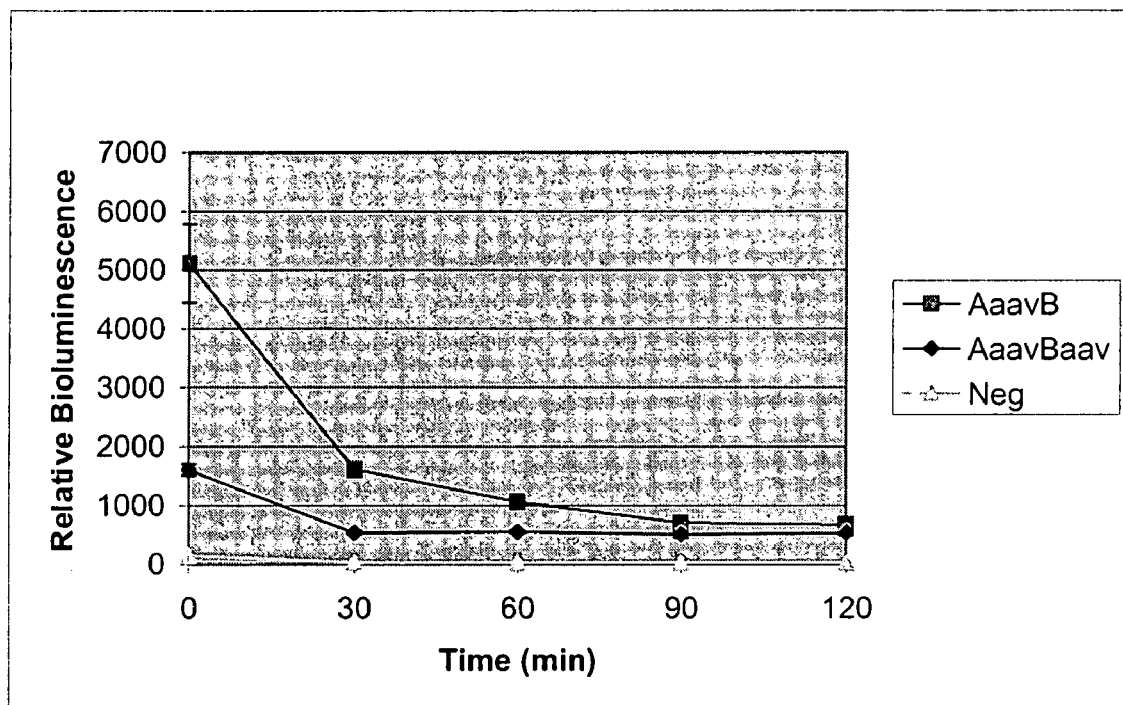
FIG. 3 is a graph showing a comparison of relative bioluminescence over time of Lux variants AaavB and AaavBaav.

FIG. 3 shows results from a separate assay in which bioluminescence was compared in the single and double variants of LuxB, i.e., pAaavB and pAaavBaav. The result shows that the behavior of the bioluminescent curve drops measurably over time for both variants, and that the rate of decline is consistent with the expected half-life of the variants.

To determine if the drop in bioluminescence output could be attributed to interference of enzymatic activity by the carboxy-terminal tag, two additional constructs were made with predicted half-lives either greater (i.e., −asv tag; 110 min.) or lesser (i.e., −laa tag; 40 min.) than those predicted for −aav tag (60 min.). The predicted half lives of these variants are also indicated in Table 2, supra. The results showed that *E. coli* containing pAasvB resulted in bioluminescence values higher than that of pAaavB ($3.35 \times 10^5$ vs. $1.3 \times 10^4$, respectively), and one third of that produced by the wild-type holoenzyme ($1.0 \times 10^6$). *E. coli* harboring pAlaaB resulted in bioluminescence measurements lower than that produced with pAaavB (i.e., $7.2 \times 10^3$ vs. $1.3 \times 10^4$, respectively), consistent with the predicted results listed in Table 2.

The results for variants containing the modified luxA genes thus indicated that: 1) a single modification of this monomer is sufficient to result in decreased half-life of the heterodimeric holoenzyme, and 2) half-life of the holoenzyme can be fine-tuned in an application-specific manner by incorporating different carboxy-terminal tags. Modification of both subunits resulted in decreased peak bioluminescence, but did not dramatically affect the half-life of the holoenzyme. Unexpectedly, modification of the LuxB monomer alone neither decreased peak bioluminescence nor resulted in decreased bioluminescence over time.

Example 4

Methods for Construction of Lux-Based Eukaryotic Bioreporter in Yeast

This example describes the construction of bioreporters in yeast cells that exhibit a reduced half life of lux-based bioluminescence relative to-control bioreporters. Reduction of the half life is based on degradation of the modified bioluminescent protein by the ubiquitin-proteasome pathway.

Genetic constructs. Using modifications of methods described above, the PEST-rich 178 carboxy terminus (C-terminus), of the G1 cyclin Cln2 (described in Berset et al., Mol. Cell Biol. 22:4463-4476, 2002; and Salama et al., Mol. Cell Biol. 14:7953-7966, 1994) was fused to the C-terminus of the *Pseudonomas luminescens* luxA and luxB genes that encode the heterodimeric luciferase (Lux AB) protein, to form modified lux A (i.e., luxAcln) and lux B (i.e., luxBcln) genes. The fused DNA sequences were cloned into a suitable yeast expression vector (i.e., pBEVY), described by Miller C A et al. 1998 *Nucleic Acids Res.* 26:3577-3583.

Bioluminescent yeast strains. Yeast cells (*Saccharomyes cerevisiae*) were transformed with constructs containing wild-type and the modified luxA and luxB genes along with the a plasmid containing luxC, luxD, luxE and frp genes. Plasmids used in this work, including pLCIRESDEIRESfrp, pUA12B7 and pGUA9B19 are described in Gupta et al. FEMS Yeast Research 4:305-313). These transformations generated *S. cerevisiae* strains able to autonomously bioluminesce.

Example 5

Lux-Based Eukaryotic Bioreporters Exhibiting Reduced Bioluminescent Half Life

The characteristics of bioluminescence emitted by transformed yeast cells constructed as described above were tested using a bioluminescence assay. In cells expressing wild-type luxA and luxBcln, inhibition of protein synthesis with the antibiotic cycloheximide led to a rapid decline in bioluminescence within 30 minutes ($t_{1/2}$). By contrast, the duration of bioluminescence emitted by cells expressing wild-type luxA and luxB was much longer ($t_{1/2}=6$ hours). Constructs containing luxAcln and the wild-type luxB did not show a significant rate of decline in bioluminescence. These data indicate that a modification of the luxB is sufficient to decrease the half-life of the bioluminescent reaction utilizing this tag.

OTHER EMBODIMENTS

This description has been by way of example of how the compositions and methods of the invention can be made and carried out. Various details may be modified in arriving at the other detailed embodiments, and many of these embodiments will come within the scope of the invention. For example, destabilized bioluminescent proteins may be expressed in eukaryotic cells other than yeast cells such as mammalian cells. Therefore, to apprise the public of the scope of the invention and the embodiments covered by the invention, the following claims are made.

---

What is claimed is:

1. A purified nucleic acid construct comprising:
    a gene cassette encoding a modified protein selected from the group consisting of:
    a modified LuxA comprising an amino acid sequence in its carboxy terminus that specifically binds to a tail-specific protease, and
    a modified LuxB comprising a PEST sequence in its carboxy terminus that specifically binds to a protein associated with a ubiquitin-proteasome pathway,
    wherein the amino acid sequence that specifically binds to a tail-specific protease results in a reduced half-life of the modified LuxA protein when expressed in a bacterial cell compared to the half-life of the wild-type form of the LuxA protein when expressed in the bacterial cell, and
    wherein the PEST sequence results in a reduced half-life of the modified LuxB protein when expressed in a yeast cell compared to the half-life of the wild-type form of the LuxB protein when expressed in the yeast cell.

2. The purified nucleic acid construct of claim 1, wherein said gene cassette encodes all proteins necessary for production of bioluminescence without addition of an exogenous substrate.

3. The purified nucleic acid construct of claim 1, wherein the modified protein is the modified LuxB and said protein associated with a ubiquitin-proteasome pathway mediates degradation of the modified LuxB via a ubiquitin-proteasome pathway.

4. The purified nucleic acid construct of claim 3, wherein said protein associated with a ubiquitin-proteasome pathway is SCF(GRR1).

5. A vector comprising the purified nucleic acid construct of claim 1.

6. The vector of claim 5, wherein said vector is a plasmid.

7. The vector of claim 5, wherein said vector is an expression vector suitable for expressing a nucleic acid incorporated in the vector in a cell type selected from the group consisting of: a bacterial cell, a yeast cell and a mammalian cell.

8. A prokaryotic cell comprising the vector of claim 5.

9. The prokaryotic cell of claim 8, wherein said cell is a bacterial cell.

10. A eukaryotic cell comprising the vector of claim 5.

11. The eukaryotic cell of claim 10, wherein said cell is a yeast cell or a mammalian cell.

12. A purified nucleic acid construct comprising a gene cassette encoding a modified LuxA comprising a carboxy-terminal sequence selected from the group consisting of SEQ ID NOS: 8, 9, and 10, wherein the half-life of the modified LuxA protein when expressed in an *E. coli* cell is shorter than the half-life of the wild-type form of the LuxA protein when expressed in the *E. coli* cell.

13. A purified nucleic acid construct, comprising a modified LuxB comprising the PEST-rich 178 amino acid carboxy terminal sequence of G1 cyclin Cln2,
    wherein the half-life of the modified LuxB protein when expressed in a yeast cell is shorter than the half life of the wild-type form of the LuxB protein when expressed in the yeast cell.

14. The purified nucleic acid construct of claim 13, wherein said gene cassette further encodes LuxA.

* * * * *

SEQUENCE LISTING

<160> NUMBER OF SEQ ID NOS: 10

<210> SEQ ID NO 1
<211> LENGTH: 29
<212> TYPE: DNA
<213> ORGANISM: Photorhabdus luminescens

<400> SEQUENCE: 1
ggtaccgcat gaaatttgga aactttttg                29

<210> SEQ ID NO 2
<211> LENGTH: 27
<212> TYPE: DNA
<213> ORGANISM: Photorhabdus luminescens

<400> SEQUENCE: 2
cccgggctaa ggagaaagaa atgaaat                  27

<210> SEQ ID NO 3

```
<211> LENGTH: 36
<212> TYPE: DNA
<213> ORGANISM: Photorhabdus luminescens

<400> SEQUENCE: 3
ttaggatcct attaggtata ttccatgtgg tacttc                                  36

<210> SEQ ID NO 4
<211> LENGTH: 73
<212> TYPE: DNA
<213> ORGANISM: Photorhabdus luminescens

<400> SEQUENCE: 4
ttacccggga ctaaactgct gcagcgtagt tttcgtcgtt tgctgcaggc ctatataata       60
gcgaacgttg ttt                                                          73

<210> SEQ ID NO 5
<211> LENGTH: 73
<212> TYPE: DNA
<213> ORGANISM: Photorhabdus luminescens

<400> SEQUENCE: 5
ttacccggga ctaagctgct aaagcgtagt tttcgtcgtt tgctgcaggc ctatataata       60
gcgaacgttg ttt                                                          73

<210> SEQ ID NO 6
<211> LENGTH: 73
<212> TYPE: DNA
<213> ORGANISM: Photorhabdus luminescens

<400> SEQUENCE: 6
ttacccggga ctaaactgat gcagcgtagt tttcgtcgtt tgctgcaggc ctatataata       60
gcgaacgttg ttt                                                          73

<210> SEQ ID NO 7
<211> LENGTH: 75
<212> TYPE: DNA
<213> ORGANISM: Photorhabdus luminescens

<400> SEQUENCE: 7
ttaggatcct attaaactgc tgcagcgtag ttttcgtcgt ttgctgcagg actggtatat       60
tccatgtggt acttc                                                        75

<210> SEQ ID NO 8
<211> LENGTH: 11
<212> TYPE: PRT
<213> ORGANISM: Artificial
<220> FEATURE:
<223> OTHER INFORMATION: 11-aa carboxy-terminal tag

<400> SEQUENCE: 8

Ala Ala Asn Asp Glu Asn Tyr Ala Ala Ala Val
1               5                   10

<210> SEQ ID NO 9
<211> LENGTH: 11
<212> TYPE: PRT
<213> ORGANISM: Artificial
<220> FEATURE:
<223> OTHER INFORMATION: 11-aa carboxy-terminal tag

<400> SEQUENCE: 9
```

```
Ala Ala Asn Asp Glu Asn Tyr Ala Leu Ala Ala
1               5                   10
```

```
<210> SEQ ID NO 10
<211> LENGTH: 11
<212> TYPE: PRT
<213> ORGANISM: Artificial
<220> FEATURE:
<223> OTHER INFORMATION: 11-aa carboxy-terminal tag

<400> SEQUENCE: 10

Ala Ala Asn Asp Glu Asn Tyr Ala Ala Ser Val
1               5                   10
```